(12) United States Patent
Pagani

(10) Patent No.: US 6,825,346 B2
(45) Date of Patent: Nov. 30, 2004

(54) PROCESS FOR THE PRODUCTION OF MELAMINE CRYSTALS AT HIGH PURENESS

(75) Inventor: Giorgio Pagani, Lugano (CH)

(73) Assignee: Casale Chemicals S.A. (CH)

( * ) Notice: Subject to any disclaimer, the term of this patent is extended or adjusted under 35 U.S.C. 154(b) by 0 days.

(21) Appl. No.: 10/220,723

(22) PCT Filed: Mar. 21, 2001

(86) PCT No.: PCT/EP01/03207

§ 371 (c)(1),
(2), (4) Date: Dec. 18, 2002

(87) PCT Pub. No.: WO01/72722

PCT Pub. Date: Oct. 4, 2001

(65) Prior Publication Data

US 2003/0149265 A1 Aug. 7, 2003

(51) Int. Cl.⁷ .................... C07D 251/60; C07D 251/62
(52) U.S. Cl. ........................ 544/201; 544/203
(58) Field of Search ................. 544/203, 201

(56) References Cited

U.S. PATENT DOCUMENTS 5,514,796 A    5/1996  Best et al.
6,380,385 B1 * 4/2002  Canzi et al. ............. 544/203

FOREIGN PATENT DOCUMENTS

| WO | WO-97/20826 A1 | 6/1997 |
| WO | WO-97/47609 A1 | 12/1997 |
| WO | WO-98/04533 A1 | 2/1998 |
| WO | WO-99/00374 A1 | 1/1999 |

OTHER PUBLICATIONS

Yanigiya et al., Tokyo Kogyo Shikensho Hokoku 57(3), 166–170, 1962.*

Crews in Ullmann's Encyclopedia of Industrial Chemistry, vol. A16, 174–179.*

* cited by examiner

*Primary Examiner*—Venkataraman Balasubramanian
(74) *Attorney, Agent, or Firm*—Akerman Senterfitt

(57) ABSTRACT

A process for producing melamine crystals at high pureness is distinguished by the fact that it comprises a crystallisation step of a flow comprising substantially pure melt melamine by cooling with liquid ammonia and a thickening step of the resulting suspension of melamine crystals in liquid ammonia by separation of a portion of the liquid ammonia present in said suspension, whereby the liquid ammonia separated in said thickening step is reused as coolant in the crystallisation step.

21 Claims, 1 Drawing Sheet

PROCESS FOR THE PRODUCTION OF MELAMINE CRYSTALS AT HIGH PURENESS

FIELD OF APPLICATION

The present invention relates to a process for the production of melamine crystals at high pureness.

More specifically, the present invention relates to a process of the non-catalytic condensation type (pyrolysis) of melt urea and subsequent crystallisation through cooling with liquid ammonia of the melt melamine so produced.

In the following description and attached claims, expressions like: "melamine (crystals) at high pureness" or "substantially pure melamine", are used to indicate a product with a concentration of melamine greater than 99%.

The invention also relates to a plant for carrying out the aforesaid process, as well as to a method for modernizing an existing plant for melamine production.

As known, in the field of melamine production, the need is more and more felt to provide a process suitable for producing in an easy, effective and reliable way melamine crystals at high pureness, whereby the process should imply low energy consumption as well as low investment, operational and maintenance costs for carrying it out.

PRIOR ART

In order to meet the above-mentioned need, processes for condensing melt urea to melamine in a non-catalytic way have been proposed in the field. Such processes operate at high pressure (80–150 bar) and the crystallisation procedure of the product therein involved is carried out in a number of steps.

During a first cooling step, ammonia (both gas and liquid) is injected for cooling the high purity melt melamine from the synthesis temperature to a temperature slightly higher than that of crystallisation, so to convert back into melamine possible degradation by-products (Melem, Melam, Melon, etc.) and counter the deammoniation of melamine during its crystallisation.

During a second cooling step, through the injection of an aqueous ammonia solution, the actual crystallisation of melamine is made occur.

Although this way of cooling the melt melamine allows obtaining a product having a high and constant pureness in time, it anyway requires suitable interventions to the cycle of mother liquors (ammonia aqueous solution), with ensuing high investment, operation and maintenance costs for the plant intended for carrying out the process.

In order to obviate to these drawbacks, processes for the production of high purity grade melamine have been proposed successively in the field, wherein the crystallisation of the melt melamine is carried out using only ammonia (gaseous and/or liquid), as coolant, without employing process water. In this way, the plant for melamine production is simplified and the investment and operation costs are reduced.

A process of this type is for example described in WO 98/0453.

Although advantageous as far as certain aspects are concerned, these process types are not always adapted for guaranteeing a product having a constant high purity and quality in time. Consequently, the so produced melamine may be used for limited uses.

Further on, the use of ammonia (gaseous and/or liquid) during the crystallisation of melt melamine as unique coolant, as it has been proposed in the prior art, implies high energy consumption and operation costs in order to separate and recover ammonia from the melamine crystals.

Because of these disadvantages, the processes according to the prior art do not allow obtaining a high quality product in an easy, reliable and economical way, notwithstanding the need more and more felt in the field.

SUMMARY OF THE INVENTION

The technical problem at the basis of the present invention is that of providing a process for the production of melamine crystals at high pureness which is simple, effective and reliable and at the same time does not require relevant investment, operation and maintenance costs and high energy consumption for carrying it out.

The above mentioned problems is solved, according to the invention, by a process of the above indicated type, which comprises the steps recited in the attached claim 1.

Preferred and advantageous embodiments of the present process are further recited in the attached claims 2–14.

As will be seen in the following, according to a preferred embodiment of the present invention, the melamine produced in a first reaction space is suitably stabilised upon removal of the vapours in a second reaction space. The second reaction space operates at the same pressure and temperature of the first reaction space in presence of gaseous ammonia at about 400° C. The so-obtained melt melamine is then cooled down quickly and crystallised at the same reaction pressure by inner circulation of liquid ammonia.

In order to carry out the aforesaid process, the present invention advantageously provides a plant for the production of melamine crystals at high pureness of the type reported in the attached claims 15–21.

According to a further aspect of the present invention, there is also provided a method for the modernization in situ of a plant for melamine production, as will described in greater detail in the description hereinbelow.

The features and the advantages of the present invention will become clear from the following indicative and non-limiting description of an embodiment of the invention, made with reference to the attached drawing.

DETAILED DESCRIPTION OF A PREFERRED EMBODIMENT

Figure 1:
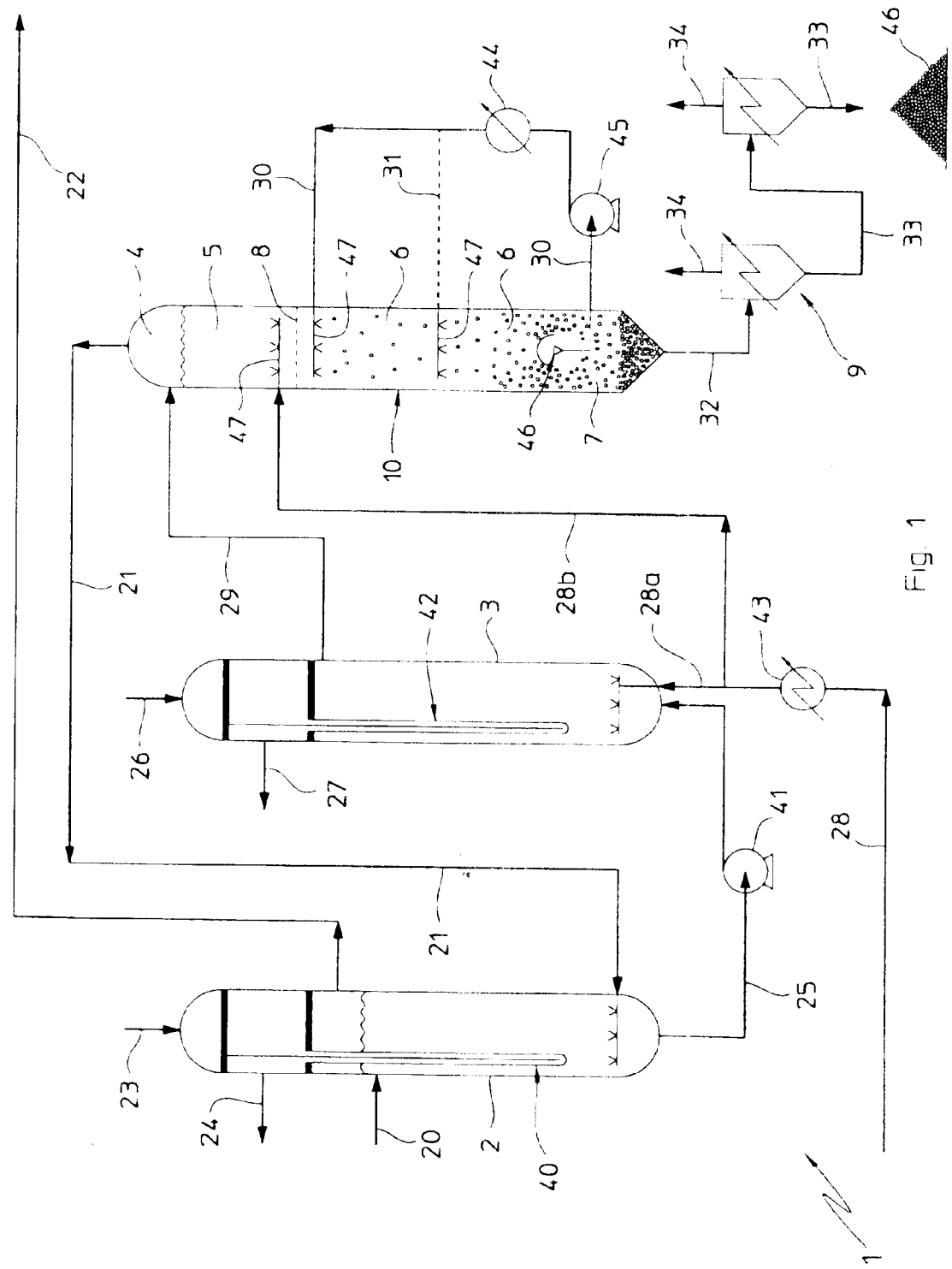
FIG. 1 shows schematically and partially a plant for the production of melamine crystals at high pureness according to a preferred embodiment of the present invention.

In FIG. 1, a plant for the production of high purity grade melamine, which is particularly adapted for carrying out the process according to the present invention, is generally referred to with numeral 1.

Plant 1 comprises a scrubbing section 2 into which a feed flow comprising melt urea (flow line 20), generally coming from a urea production plant (not shown) at a temperature of 135–140° C., is introduced.

The scrubber 2 operates at a pressure of 140–180 bar (preferably 160 bar).

The melt urea fed to the scrubbing section 2 meets in counter-current and in bubbling phase the off-gases comprising $NH_3$ and $CO_2$ and melamine vapours coming (flow line 21) from a separation section 4. Such off-gases preferably have a temperature of about 400° C.

All the melamine and a small part of $NH_3$ and $CO_2$ are condensed and dissolved in the melt urea. The residual off-gases are separated and vented by the scrubber 2 through the flow line 22, to be recovered in a conventional way in the urea plants (not shown).

The excess heat is taken out producing steam (flow lines 23 and 24) through indirect heat exchange with water in a heat exchanger schematically shown at 40, for example of the bayonet-tube type. In this way, the urea temperature inside the scrubber 2 is controlled so not to rise above 230–240° C., in such a way to avoid the formation of undesired compounds such as biuret, triuret, etc.

The melt urea coming from the scrubbing section 2 is sent through the flow line 25 to a first reaction space 3. At numeral 41 a pump is schematically represented for feeding such melt urea flow to the reaction space 3.

The reaction space 3 comprises a reactor with an outer cylindrical shell and a tube bundle heat exchanger 42 inside it, for example of the bayonet-tube type.

Inside the reaction space 3 the operating pressure is preferably higher than that for urea synthesis in order to permit an economical and easy recovery of the off-gases generated during melamine production.

For example, the melamine is produced at a pressure of 140–180 bar (preferably 160 bar), nearly at the same pressure of the scrubber 2, and at a temperature of 350–450° C., preferably 400° C.

The reactant residence time is 60–120 minutes (preferably 90 minutes); such residence time is calculated in such a way to obtain a substantially complete condensation reaction from urea to melamine.

The heat necessary for the condensation from urea to melamine (a strongly endothermic pyrolysis reaction) is generally provided by indirect heat exchange with melt salts (flow lines 26 and 27) or other heating means.

A certain amount of gaseous ammonia, preheated at about 400° C. in the heat exchanger 43, is introduced at the bottom of the first reaction space 3 through the flow lines 28, 28a. This to guarantee the melt urea a certain turbulence, enhance the heat exchange and increase the ammonia partial pressure, which is useful in view of the product stability.

A flow comprising melt melamine and ammonia, carbon dioxide and melamine vapours, exits from the first reaction space 3 and is directed through the flow line 29 to the first separation section 4.

The first separation section 4 comprises a separation chamber wherein the separation of the flow comprising melt melamine from the ammonia, carbon dioxide and melamine vapours takes place.

Section 4 operates at a pressure of 140–180 bar (preferably 160 bar). The vapours separated from melt melamine are sent through the flow line 21 to the scrubbing section 2, whereas the flow comprising melt melamine is fed to the second reaction space 5.

Advantageously, according to a preferred embodiment of the present invention, the separation section 4, the second reaction space 5, the crystallisation section 6 and the thickening section 7 (these two last sections will be described in greater detail in the description hereinbelow) are adjacent to each other inside the same apparatus, generally indicated with 10.

In the second reaction space 5 (also called "digester" in the jargon of the field), the flow of melt melamine, after the separation of the vapours, is stripped with a gaseous flow comprising ammonia having a higher temperature than the melamine crystallisation temperature, preferably about 400° C. (flow line 28b).

In this way it is possible to convert possible degradation by-products (Melem, Melam, Melon, etc.) present in the flow comprising melt melamine fed to the second reaction space 5, so allowing obtaining substantially pure melamine.

Advantageously, the pressure in the second reaction space 5 is substantially equivalent to that of the first reaction space 3, that is to say about 140–180 bar (preferably 160 bar). The same applies for the temperature: 350–450° C., preferably 400° C.

Further on, particularly satisfying results have been found with a residence time of the melt melamine in the second reaction space 5 equal to about 20–60 minutes, preferably 30 minutes.

In doing so, not only are the last traces of carbon dioxide stripped and the temperature maintained at the same value of the first reaction space 3, but—in absence of carbon dioxide—also the ammonia partial pressure is increased with respect to that of the first reaction space 3, in an amount equal to that of the $CO_2$ partial pressure in the first reaction space 3.

These results may be obtained by making the gaseous flow comprising ammonia to flow both in counter-current with respect to the melt melamine flow in the reaction space 5, as shown in FIG. 1, or in co-current with the same.

Important is that a suitable mixing take place between the gaseous ammonia and the melt melamine.

The reaction space 5 may further be provided in an independent reactor (not shown) in fluid communication with the separation section 4 and the crystallisation section 6.

The crystallisation section 6 is fed with a flow comprising substantially pure melt melamine, which is obtained in the second reaction space 5.

The crystallisation section 6 is separated from the second reaction space 5, in the example of FIG. 1, by means of a perforated plate 8, and advantageously operates at the same operative conditions as such reaction space, preferably at about 400° C. and 160 bar.

Further on, a flow which comprises liquid ammonia as coolant, for example at a temperature comprised between 30 and 60° C., preferably 40° C., is fed to the crystallisation section 6 through the flow line 30.

The cooling and the successive crystallisation of melamine take place, under isobaric conditions, through mixing with said liquid ammonia.

According to a particularly advantageous embodiment of the present invention, shown in FIG. 1, the cooling liquid ammonia is at least in part comprised of a flow comprising recycled liquid ammonia (flow line 30) coming from the thickening section 7, that will be described in the following.

Inside the crystallisation section 6, ammonia and melt melamine are mixed so to let the melamine crystallise by cooling and to obtain a suspension of melamine crystals in liquid ammonia. In this respect, the mixing between the flow comprising substantially pure melt melamine and the flow comprising liquid ammonia takes place by making such flows to flow inside said crystallisation section 6 in co-current.

The perforated plate 8 has—inter alias—the task of splitting the flow comprising melt melamine in a plurality of flows inside the section 6, so to enhance an optimal distribution and capillary mixing of melamine with the coolant.

Preferably, the amount of ammonia is set in such a way to have as final product a suspension of melamine crystals in liquid ammonia at about 80–120° C., preferably 100° C.

In other words, liquid ammonia serves as heat carrier. Thanks to the cooling rapidity and the operating high pressure in the chrystallizer 6 (and hence of ammonia), the melamine is nearly completely stabilised with the suppression of the tendency to form undesirable degradation by-products, thus a highly pure product being obtainable.

At the bottom of the crystallisation section 6, a "theoretical" suspension may be for example obtained of about 10% weight of melamine in liquid ammonia.

According to an advantageous aspect of the present invention, the suspension of melamine in liquid ammonia from section 6 is fed to a thickening section 7 that operates at the same pressure and temperature conditions of section 6.

In section 7, a portion of the liquid ammonia is advantageously separated and at least partly recycled to the crystallisation section 6 through the flow line 30, as shown in FIG. 1.

Before being fed to the crystallisation section 6, the recycled ammonia flow is advantageously cooled down to a temperature of about 30–60° C., preferably 40° C., by means of suitable cooling means, shown in FIG. 1 by the heat exchanger 44. Moreover, with numeral 45 a pump is indicated for recycling the liquid ammonia to section 6.

Given the relevant different of specific weight between the melamine crystals ($Y \cong 1.57$ kg/dm$^3$) and liquid NH$_3$ ($Y \cong 0.45$ kg/dm$^3$), it is advantageously possible to realise a separation (thickening), at least coarse, between the solid (melamine crystals) and the liquid (ammonia). Such a separation may be achieved, for example, by gravity, by (gentle) centrifugation or by filtration.

At the bottom of the thickening section 7 (conical zone of the apparatus 10) a slurry of melamine crystals is obtained, which is fed through the flow line 31 to a second separation section generally indicated with numeral 9 that will be described in the following in greater detail.

Particularly satisfying results have been obtained by extracting from the melamine crystals suspension an amount of liquid ammonia such to produce a slurry (on the bottom of section 7) having a concentration of melamine equal to about 50% in weight.

The flow of liquid ammonia is extracted from the melamine crystal suspension and hence from section 7, at an end portion of the same by means of suction means generally indicated with numeral 46. Such means are in fluid communication with the feed flow line 30 for the liquid ammonia to the crystallisation section 6.

According to a further particularly advantageous aspect of the present invention, the flow of liquid ammonia extracted from the melamine crystal suspension in the thickening section 7, may further comprise melamine micro-crystals in suspension.

Indeed, it has been surprisingly found that the presence of micro-crystals in the liquid ammonia (flow line 30) recycled to the crystallisation section 6 allows optimising the melamine crystallisation process. In fact, such micro-crystals advantageously act as "crystallisation seeds" thus allowing obtaining a product of high quality even from the viewpoint of the crystal granulometry.

According to a preferred embodiment of the present invention, the feed of the recycle liquid ammonia flow (comprising in case being even melamine micro-crystals) may be carried out in a plurality of zones inside the crystallisation section 6. In this way, it is possible to optimally control the progression of crystallisation.

In the example of FIG. 1, such feeding may be carried out in two zones (an upper and an intermediate zone, respectively) of section 6, as shown by the flow lines 30 and 31.

Finally, the slurry of melamine crystals (for example 50% melamine and 50% NH$_3$) is supplied through the flow line 32 to the second separation section 9, comprising in the example of FIG. 1 two flash separators. Here the ammonia still present is separated, so as to obtain melamine crystals at high pureness substantially free of ammonia.

In other words, the melamine slurry is processed in a finishing step (9), in order to completely remove ammonia.

Such operation of ammonia separation in section 9 takes place through instantaneous expansion of the melamine slurry and ensuing evaporation of ammonia.

The melamine crystals which are more and more getting dry and poor in ammonia content pass through the different separation steps of the section 9 through flow line 33 whereas ammonia exits from such steps as vapour through the flow lines 34.

The end product obtained thanks to the process according to the present invention is indicated with numeral 46.

Distributors of gaseous and liquid ammonia, respectively, which are provided inside apparatus 10 at the sections 5 and 6, are indicated with numeral 47.

Advantageously this last separation step is enhanced by the presence of a melamine crystal slurry, instead of a melamine crystal suspension as it is the case in the prior art.

Preferably, the separation takes place in a plurality of separation steps (flash separators in FIG. 1), operating at decreasing pressures up to reach the atmospheric pressure (the number of separation steps may preferably vary from 2 to 5.6). The product temperature is suitably controlled by means of conventional techniques through heat provided by means of heat exchange.

It shall be noted that the pressure drop from 160 bar to about 18–20 bar (pressure in the first flash separator) has no effect on the product stability, the product being at the solid state quite distant from the melting point. Therefore, in this step, there is no undesired production of degradation by-products, differently from what occurs in other processes of the prior art.

A number of advantages are obtained thanks to the present invention. It is worth mentioning that thanks to the presence of a melamine crystallisation and thickening step, with respective recycle of the coolant, the energy consumption and the investment, operation and maintenance costs associated to the separation of ammonia from the suspension of melamine crystals are substantially lower than in the processes of the prior art.

In fact, the crystallisation step through mixing with recycled liquid ammonia coming from the thickening section, allows minimising the amount of ammonia to be let evaporate in the subsequent low pressure separation step, with relevant energy and investment savings.

As a conclusion, the high energy consumption and operation costs associated with the separation through expansion at low pressure (about 1–20 bar) of large amounts of liquid ammonia present in the suspension of melamine crystals in order to obtain the end product, and associated to the subsequent condensation and recycle step at high pressure (140–180 bar) to the crystallisation section of the separated ammonia, present in the processes according to the prior art, are substantially reduced by the process according to the present invention.

In the plant of FIG. 1, the means for feeding, connecting and recycling the various compounds to and from the different sections 2–9 not previously described, are for example embodied by pipes, tubes, valves and other components, which have not been shown because in se conventional.

The plant exemplified in FIG. 1 may be a brand new plant or obtained by modernizing an existing plant.

In an existing plant such modernisation advantageously foresees the provision of a second reaction space, of a crystallisation section, of a thickening section and respective coolant recycles such as previously described with reference to FIG. 1.

What is claimed is:

1. Process for the production of melamine crystals at high pureness comprising the steps of:
   feeding a flow comprising substantially pure melt melamine and a flow comprising liquid ammonia as coolant in a crystallisation section;
   mixing said flow comprising substantially pure melt melamine and said liquid ammonia in said crystallisation section thus obtaining a suspension of melamine crystals in liquid ammonia;
   feeding said suspension of melamine crystals in liquid ammonia to a thickening section;
   extracting in said thickening section a portion of said liquid ammonia from said suspension of melamine crystals, thus obtaining a slurry of melamine crystals;
   recycling to said crystallisation section at least a portion of said liquid ammonia extracted in said thickening section;
   feeding said slurry of melamine crystals to a separation section in order to remove the liquid ammonia still present and obtain melamine crystals at high pureness substantially free of ammonia.

2. Process according to claim 1, characterized in that said flow comprising substantially pure melt melamine is obtained by the steps of:
   condensing a flow comprising melt urea in a first reaction space, thus obtaining a flow comprising melt melamine and ammonia, carbon dioxide and melamine vapours;
   feeding said flow comprising melt melamine and ammonia, carbon dioxide and melamine vapours to a separation section for separating the melt melamine from the vapours;
   feeding a flow comprising melt melamine obtained in said separation section and a gaseous flow comprising ammonia having a temperature higher than the melamine crystallization temperature to a second reaction space for converting to melamine possible degradation by-products present in the flow comprising melamine, thus obtaining a flow comprising substantially pure melt melamine.

3. Process according to claim 1, wherein said crystallisation section and said thickening section operate at substantially the same pressure as the synthesis pressure of the substantially pure melt melamine.

4. Process according to claim 2, wherein said first and second reaction space, said crystallisation section and said thickening section all operate at a substantially equivalent pressure.

5. Process according to claim 2, wherein said first and second reaction space operate at a substantially equivalent temperature.

6. Process according to claim 2, wherein the residence time of the reactants in said first and second reaction space is between 60 and 120 minutes, and between 30 and 90 minutes, respectively.

7. Process according to claim 1, wherein the liquid ammonia fed to said crystallisation section has a temperature between 30 and 60° C.

8. Process according to claim 1, further comprising a cooling step of said at least a portion of liquid ammonia extracted in said thickening section before having it recycled to said crystallisation section.

9. Process according to claim 1, wherein the flow comprising liquid ammonia as coolant fed to the crystallization section is the flow of recycled liquid ammonia coming from said thickening section.

10. Process according to claim 1, wherein said extraction step in said thickening section of a portion of the liquid ammonia from said suspension of melamine crystals occurs by at least one of gravity, centrifugation and filtration.

11. Process according to claim 1, wherein the slurry of melamine crystals obtained in said thickening section comprise about 50% in weight of melamine and about 50% in weight of liquid ammonia.

12. Process according to claim 1, wherein the flow comprising liquid ammonia as coolant is fed to a plurality of zones of said crystallisation section.

13. Process according to claim 1, wherein said mixing between the flow comprising substantially pure melt melamine and the flow comprising liquid ammonia is accomplished by making said flows to flow in co-current inside the crystallisation section.

14. Process according to claim 1, wherein said flow of liquid ammonia recycled to said crystallisation section further comprises micro-crystals of melamine in suspension.

15. Process according to claim 4, wherein said substantially equivalent pressure is between 140 and 180 bar.

16. Process according to claim 4, wherein said substantially equivalent pressure is 160 bar.

17. Process according to claim 5, wherein said substantially equivalent temperature is between 350 and 450° C.

18. Process according to claim 5, wherein said substantially equivalent temperature is 400° C.

19. Process according to claim 6, wherein the residence time of the reactants in said first reaction space is 90 minutes.

20. Process according to claim 6, wherein the residence time of the reactants in said second reaction space is 60 minutes.

21. Process according to claim 7, wherein the liquid ammonia fed to said crystallisation section has a temperature of 40° C.

* * * * *